United States Patent [19]

Sick

[11] 4,116,527
[45] Sep. 26, 1978

[54] DEVICE FOR CONCENTRATING LIGHT FROM A LINEAR FIELD ON TO A RECEIVER

[75] Inventor: Erwin Sick, Icking, Fed Rep. of Germany

[73] Assignee: Erwin Sick Gesellschaft mit beschrankter Haftung Optik-Elektronik, Waldkirch, Fed Rep. of Germany

[21] Appl. No.: 738,340

[22] Filed: Nov. 3, 1976

[30] Foreign Application Priority Data

Nov. 12, 1975 [DE] Fed. Rep. of Germany ....... 2550815

[51] Int. Cl.² ............................................. G02B 27/17
[52] U.S. Cl. ...................... 350/6.7; 350/6.6; 350/6.9; 356/200
[58] Field of Search ................. 350/6, 7, 55, 96 WG, 350/96 R, 286, 299, 294, 301, 175 TS; 356/199, 200; 358/305, 285

[56] References Cited

U.S. PATENT DOCUMENTS

| 3,062,965 | 11/1962 | Sick | 350/7 |
| 3,758,197 | 9/1973 | Klang et al. | 350/286 |
| 3,762,794 | 10/1973 | Arnaud | 350/301 |
| 3,998,554 | 12/1976 | Burch et al. | 350/175 TS |
| 4,033,678 | 8/1977 | Rudd | 350/301 |
| 4,052,120 | 10/1977 | Sick | 350/105 |

FOREIGN PATENT DOCUMENTS 604,161  6/1948  United Kingdom .................... 350/190

OTHER PUBLICATIONS

L. B. Richards, Photodetector as Function Detector, Aug. 1970, I.B.M. Technical Disclosure Bulletin, vol. 13, No. 3, Aug. 1970.
D. H. Cronquist, Hollow Reflecting Light Collector Tube, Aug. 1974, IBM Technical Disclosure Bulletin.

*Primary Examiner*—John R. Corbin
*Assistant Examiner*—B. W. de los Reyes

[57] ABSTRACT

An apparatus for concentrating light from a linear field on to a relatively small receiver disposed at the end of a rod light guide on the peripheral surface of which light emanating from the linear field is directed. The linear field is arranged substantially at the focal distance from a first concave strip mirror which is disposed so as to extend optically parallel to the field and reflects the incident light from the field to a second concave strip mirror which is optically parallel with the first mirror and forms therewith a substantially telecentric system and which, in turn, reflects the incident light to the peripheral surface of the rod light guide.

17 Claims, 5 Drawing Figures

DEVICE FOR CONCENTRATING LIGHT FROM A LINEAR FIELD ON TO A RECEIVER

The invention relates to a device for concentrating light coming from a linear field on to a relatively small receiver with a rod light guide on to the peripheral surface of which light coming from the linear field is directed, and at the end of which the receiver is disposed.

It is already known to use a rod light guide to concentrate light from a linear field, i.e., one extending mainly in one direction, by way of the rod light guide on to a receiver, preferably a photoreceiver, disposed at one or both ends of the rod light guide. This utilizes the property of a rod light guide to conduct internally to the ends, light striking its peripheral surface and scattered at the angle of total reflection. Devices of this kind are used in line scanning devices, for example, wherein for example a laser beam is guided periodically by a mirror wheel over a web of material which is to be examined. Here the light sent back, or reflected, from the web may be guided, by way of a cylindrical lens extending parallel to the scanning direction, directly into the rod light guide which is disposed in front of it. It is often difficult, however, to dispose a rod light guide in the vicinity of the linear field emitting the light, especially in the case of a web of material which is moved forward continuously, for example in a sheet rolling mill, and the optical elements for the light transmitting part already have to be disposed close to the web.

The aim of the invention is, therefore, to provide a device of the type mentioned with which it is possible to dispose the rod light guide with the photoreceiver at one or both ends, at a considerable distance from the linear field without having to make disproportionate sacrifices in luminous efficiency. The achievement of high luminous efficiency is the reason why the rod light guides have hitherto been placed as close as possible to the linear scanning field and, for example, autocollimation beam paths known from other optical fields have been abandoned.

As a solution of this problem the invention provides for the linear field to be disposed somewhat within the range of the focal length of a concave strip mirror, extending optically parallel to the field, which reflects the incident light to a further concave strip mirror, optically parallel to it and forming with it a telecentric system, which in turn reflects the incident light to the peripheral surface of the rod light guide. The fact that the first concave mirror is disposed close to the linear field ensures that a large part of the scattered light emanating from the field is picked up. The use of a second concave mirror forming a telecentric system with the first ensures, further, that the light striking the first concave mirror reaches the second concave mirror, almost completely, also. The parallel beam leaving this concave mirror then strikes the peripheral surface of the rod light guide extending parallel to it, and is thus likewise picked up almost completely by the rod light guide and so passed on for evaluation. Thus the rod light guide, including the photoreceiver in the form of a photomultiplier, can be accommodated in the interior of the device at a most convenient point, for example for the placing of the auxiliary electronic equipment.

The focal lengths of the first and second concave mirrors are advantageously in the ratio 2:1 to 8:1, preferably 4:1. The concave mirrors may either be spherical mirrors or cylindrical mirrors, co-operating with a cylindrical lens extending normally to the axis of the cylinder, the axis of which cylindrical mirrors extends optically normal to the direction of the linear field.

Particular advantage is gained from the use of a rod light guide carrying on the peripheral side diametrically opposite the incidence of light a stepped mirror arrangement which reflects light arriving substantially normal to the axis of the rod at angles of total reflection in the rod. A stepped mirror arrangement of this type on a rod light guide has been described already in German patent application No. P 25 08 366.3. The stepped mirrors reflect the light falling substantially perpendicularly to the axis of the rod back into the rod at angles such that the reflected rays strike the peripheral surface of the rod at angles of total reflection and so are reflected towards the ends where there is provided either a mirror coating or a photoreceiver. The rod light guide preferably has a round cross-section so that light striking the peripheral surface is concentrated in the region of the stepped mirror arrangement.

It is convenient if the stepped mirror arrangement takes up only a part, preferably half, of the length of the rod light guide and is disposed advantageously symmetrically with respect to the middle of the rod. This construction produces a certain homogenisation of the reflected light in the region of the ends of the rod because there the stepped mirror arrangement can no longer have a disturbing effect with the backwards and forwards reflection of the light rays in the rod. At the end of the rod light guide which carries the photoreceiver it is also possible to dispose an Ulbricht globe, at the output side of which is the photoreceiver. An arrangement of this kind is described in our copending application (ref. German application No. P 25 50 814.9 of the same priority date) entitled "Line Scanning Device for webs of material for the detection of faults".

A particularly preferred application of the invention is in a device wherein the linear field is the scanning range of a light spot which is formed by a laser, a light deflecting device and an imaging system with a concave mirror. The light deflecting device, preferably a mirror wheel, is located here substantially at the focal point of the concave mirror and produces a light spot scanning the linear field in its longitudinal direction.

According to an embodiment of the invention it is also provided, in a device of this kind, that the first concave mirror shall simultaneously be used for imaging the light spot and the receiving beam shall be separated from the transmitted light beam before entry into the light deflecting device and guided to the second concave mirror. Thus the concave mirror which is known for producing a scanning light spot in line scanning is utilized simultaneously, in the form of an autocollimation beam path, to conduct the receiving light beam to the second concave mirror, the above defined separation of receiving and transmitted light beam being particularly important in achieving a high luminous efficiency. Thus the invention operates with a pupil division and preferably ⅓ of the beam cross-section is utilized for the transmitted light beam and ⅔ of the light beam cross-section for the receiving light beam.

A further form of construction is characterised in that the transmitted light beam and the receiving light beam are conducted between the light deflecting device, or the second concave mirror, and the first concave mirror by way of mutually tilted plane mirrors. As a result of this measure the separation of the receiving and the transmitted light beams can be carried out even before the light deflecting device. With the known autocollimation beam paths the separation of transmitted and receiving light beams was not performed until the transmission side of the light deflecting device was reached, with the result that the luminous efficiency was inadequate.

A very compact construction is obtained if the transmitted light beam is reflected back by the light deflecting device slightly obliquely to a strip mirror system, consisting of the two narrow plane mirrors tilted with respect to one another. The transmitted light beam can be further reflected by the mirror system to another narrow plane mirror which guides the beam back to the first concave mirror which may be located approximately level with the light deflecting device.

The invention is described below by way of example with reference to the accompanying drawings in which the Figures are as follows.

Figure 1:
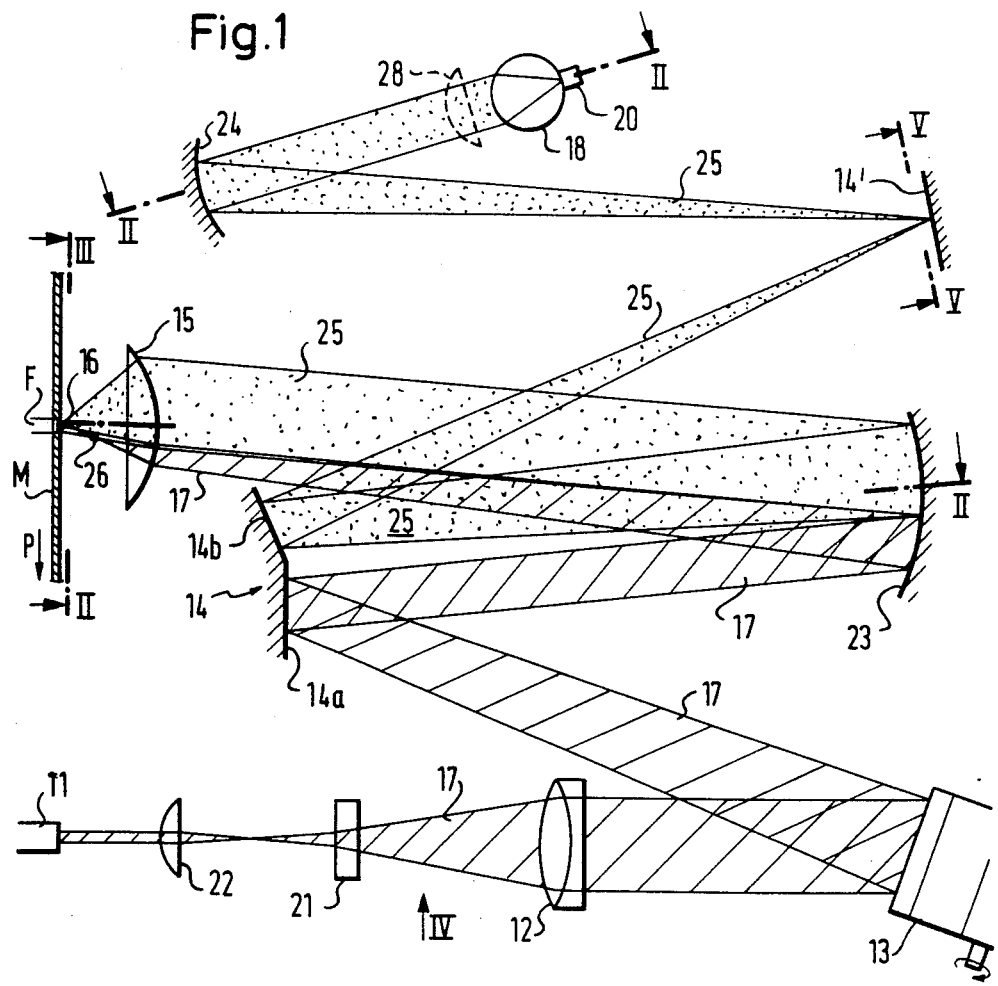
FIG. 1 is a schematic elevation of a preferred line scanner according to the invention with quasi-autocollimation receiving beam path.
Figure 4:
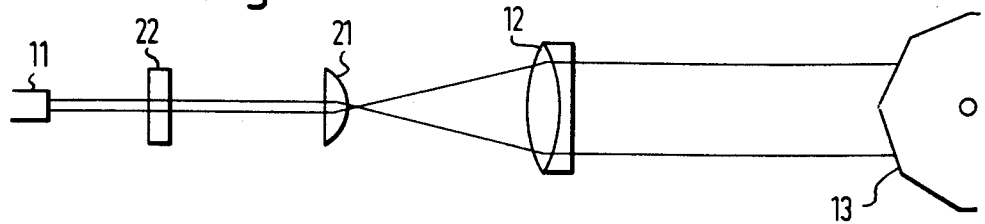
FIG. 4 is an elevation of the transmitting beam path as far as the mirror wheel in the direction of the arrow IV in FIG. 1.

As shown in FIGS. 1 and 4, the very narrow and coherent light beam of a laser 11 is dispersed fanwise by crossed cylindrical lenses 21, 22, the focal lengths of which are approximately in the ratio 1:10, so that an objective 12 is fully illuminated. The position of the axes of the cylindrical lenses relative to a mirror wheel 13 is as represented in FIG. 1. The objective 12 is disposed with its focal point approximately in the position of the focal line of the cylindrical lens 21, so that in the plane of FIG. 4 it produces a parallel light beam which falls on to the mirror wheel 13 which is tilted with its axis as shown in FIG. 1. The result is a transmitted light beam 17. The transmitted light beam 17 is guided by the mirror wheel 13 to a plane mirror 14a which in its extension perpendicular to the plane of the drawing is striplike in form. The plane mirror 14a reflects the transmitted light beam 17 to a concave mirror 23 the focal point of which lies on the surface of the mirror wheel 13 and which, together with the objective 12 and a cylindrical lens 15, focusses the transmitted light at a point 26 located immediately in front of a web of material M. The mirror 23 may be a spherical mirror or a cylindrical mirror with an axis perpendicular to the plane of FIG. 2, to which axis of the cylindrical lens 15 is perpendicular.

Figure 3:
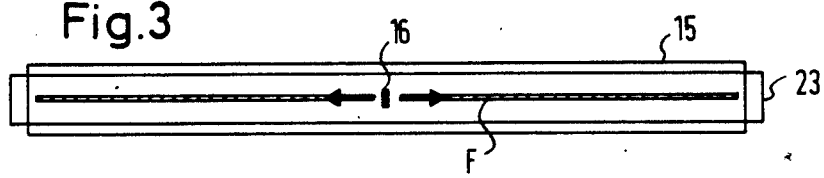
FIG. 3 is a schematic elevation in the direction of the line III—III of FIG. 1.

As a result of this construction the laser 11 produces on the web of material a line of light 16 which, when the mirror wheel 13 is rotated, as shown in FIG. 3, scans the linear field F in the direction of the double arrow, on the web of material M transversely to its longitudinal extension. Here, the web of material may move in the direction of the arrow P in FIG. 1 so as to ensure a line scanning and consequently a continuous detection of faults. Hence the line of light is directed in the running direction P of the web.

The receiving beam path 25 starts at the line of light 16. The receiving light beam 25 emanating from this spot and occupying approximately ⅔ of the beam path cross-section is guided by way of the concave mirror 23 to a further plane mirror 14b which, with the mirror 14a, forms a bent mirror system 14, i.e., in the invention the plane mirror 14b is tilted relative to the plane mirror 14a about an axis which is perpendicular to the plane of the drawing in FIG. 1 so that the receiving light beam 25 is guided, not to the mirror wheel 13 but by way of a further plane mirror 14' to a further concave mirror 24.

Figure 2:
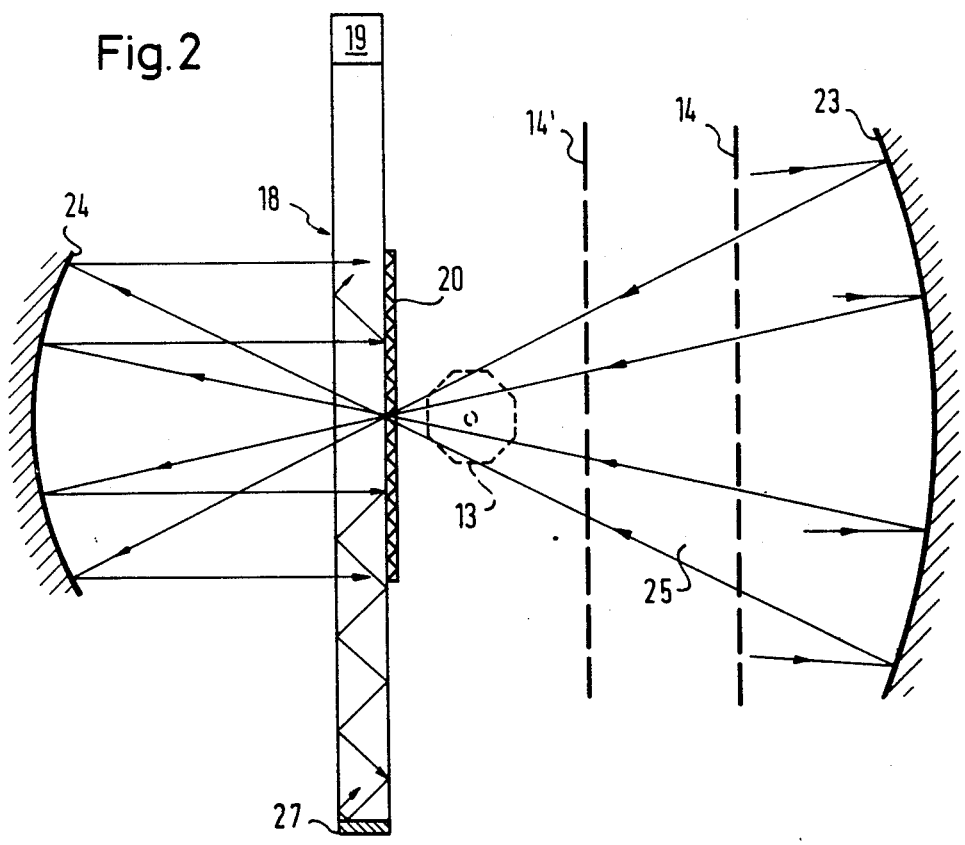
FIG. 2 is a schematic section taken along the middle axis of the receiving light beam of FIG. 1 as shown by the line II—II, the bent beam paths resulting from reflection at plane mirrors being shown extended for the purpose of simplicity.

As can be seen from FIGS. 1 and 2, the focal point, or focal line, of the concave mirror 24 coincides with the focal point, or focal line, of the concave mirror 23. In the example of construction this point lies on the plane mirror 14'. Thus the receiving light beam 25 is reflected from the concave mirror 24 as a substantially parallel beam which, possibly by way of a further cylindrical lens 28, meets the peripheral surface of a rod light guide 18. Here, the concave mirror 24, and if applicable the cylindrical lens 28, can be so arranged that the light beam refracted by the rod light guide is also concentrated on a stepped mirror system 20 which is disposed on the peripheral surface opposite the light incidence side and extends in the longitudinal direction of the rod light guide 18. The stepped mirror system 20 reflects the incident light in such a way that it is conducted by total reflection in the rod light guide to the ends of the rod. A mirror coating 27 is provided at one end which reflects incident light back into the rod. At the other end is a photomultiplier 19 which emits an electric signal corresponding to the intensity of the incident light, which can be employed, for example, for the evaluation of faults.

The manner of operation of the device according to the invention is as follows.

The scatter light emanating from the linear field F is largely picked up by the cylindrical lens 15 and the concave mirror 23. By deflection of the receiving light beam 25 by means of the tilted plane strip mirror 14b, the light which has been picked up is conducted almost completely to the concave mirror 24 which then directs the light, again almost completely, into the rod light guide 18.

To obtain a certain degree of homogenisation of the light reaching the photoreceiver 19 only the middle portion of the rod light guide 18 is provided with the stepped mirror system 20, as shown in FIG. 2, the ends remaining available for the homogenisation of the light. Thus there is a light intensity sufficient to produce an electric signal well above the background noise existing at the photoreceiver even when the web of material consists of paper or fabric which, in contradistinction to metal, scatters back only a relatively small part of the incident light. The device operates satisfactorily with metal also, the line of light 16 being particularly advantageous.

The transmitted beam path 17 can, moreover, be of such a nature as is described in the patent application entitled "Line scanning device (our reference S 3124)" which is being filed simultaneously.

It is advantageous to use a mirror wheel with 16–20 reflecting surfaces.

Figure 5:
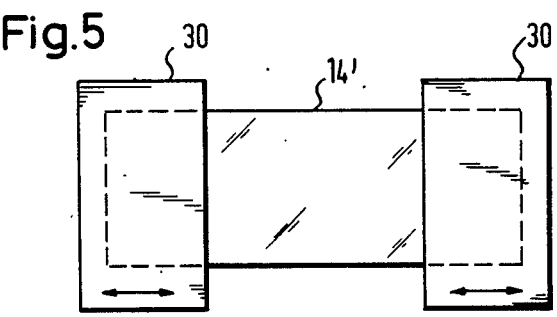
FIG. 5 is an elevation along the line V—V in FIG. 1.

FIG. 5 shows that the mirror 14' bounded on both sides by diaphragms 30 which can be slid in the direction of the double arrows; this ensures, especially in the case of webs of material which scatter light widely, that the concave strip mirror 24 picks up all the light reflected by the mirror 14' in every phase of the scanning process.

The optical elements 14, 14', 23, 24 are all more or less elongated, or lamellar, in the scanning direction.

The telecentricity of the optical system consisting of the mirrors 23, 24 is in general not critical. What is decisive is that the light from the concave mirror 24 falls on the stepped mirror system at such angles, even in the case of deviations from exact parallelism, that the reflected rays in the rod 18 still strike the wall at angles of total reflection. A certain deviation from exact telecentricity with a ray divergence of around 10°–15° even has the advantage that a plurality of devices can be disposed side by side without a break in a row. Of course if it is also required to detect holes in a web of paper which is running over a surface giving specular reflection an exactly telecentric beam path is necessary.

What is claimed is:

1. An apparatus for concentrating light from a linear field onto a relatively small receiver, comprising: a rod light guide with a peripheral surface, said receiver being disposed at the end of said rod light guide on the peripheral surface of which light emanating from the linear field is directed, a first concave strip mirror, said linear field being arranged substantially at the focal distance from said first concave strip mirror, said mirror being disposed so as to extend optically parallel to the field, and a second concave strip mirror, said first mirror reflecting the incident light from said field to said second concave strip mirror, said second mirror being optically parallel with the first mirror and forming therewith a substantially telecentric system and reflecting the incident light to the peripheral surface of the rod light guide, and a stepped mirror system carried by said light guide on that side of its periphery diametrically opposite the incident light, said stepped mirror system reflecting back, at angles of total reflection in the rod, incident light which strikes substantially perpendicularly to the axis of the rod.

2. Apparatus according to claim 1, wherein the ratio of the focal length of the first concave mirror to that of the second concave mirror is from 2:1 to 8:1.

3. Apparatus according to claim 2, wherein said ratio is about 4:1.

4. Apparatus according to claim 1, wherein said concave mirrors are spherical mirrors.

5. Apparatus according to claim 1, wherein said concave mirrors are cylindrical mirrors co-operating with a cylindrical lens extending peripendicularly to the axis of the cylinder, the axis of the cylindrical mirrors being optically perpendicular to the direction of the linear field.

6. An apparatus according to claim 5, wherein said cylindrical lens is arranged in front of said rod light guide.

7. Apparatus according to claim 1, wherein the stepped mirror system occupies only part of the length of the rod light guide.

8. Apparatus according to claim 7, wherein the stepped mirror system is arranged symmetrically about the middle of the rod.

9. Apparatus according to claim 1, wherein said linear field is the scanning range of a light spot, comprising means for forming said light spot including a laser, a light deflecting device and an imaging system with a concave mirror, said first concave mirror serving simultaneously for imaging the line of light and the received light beam is separated from the transmitted light beam between said first concave mirror and the light deflecting device and is guided to the second concave mirror.

10. Apparatus according to claim 9, comprising two plane mirrors for guiding the transmitted beam between the deflecting device and the first concave mirror, and for guiding the received beam between the first concave mirror and the second concave mirror, respectively, said two plane mirrors being tilted relative to each other.

11. Apparatus according to claim 10, comprising a bent strip mirror arrangement and wherein the transmitted light beam is reflected by the light deflecting device slightly obliquely to said bent strip mirror arrangement which comprises said respective plane mirrors.

12. Apparatus according to claim 11, wherein a third plane mirror is located between the bent mirror arrangement and the second concave mirror.

13. Apparatus according to claim 12, wherein the focal point of the second concave mirror lies on said third plane mirror.

14. Apparatus according to claim 12, comprising diaphragms and wherein the third plane mirror is adapted to be masked at the ends by said diaphragms.

15. Apparatus according to claim 9, wherein approximately ⅓ of the autocollimation beam path produced by pupil division is employed for the transmitted light beam and approximately ⅔ for the received light beam.

16. Apparatus according to claim 1, wherein said rod light guide has a second side opposite said side and has a longitudinal axis, and wherein said stepped mirror system comprises a plurality of mirrors inclined with respect to said longitudinal axis and arranged substantially exactly one behind the other when looking in the direction of said axis such that light reflected by said mirrors impinges on said second side at angles of total reflection.

17. An apparatus according to claim 1, wherein said rod light guide has a circular cross section.

* * * * *